(12) United States Patent
Schneider et al.

(10) Patent No.: US 11,162,920 B2
(45) Date of Patent: Nov. 2, 2021

(54) SAMPLE PREPARATION FOR PROTEOMIC INVESTIGATIONS

(71) Applicant: FEDERAL REPUBLIC OF GERMANY LAST REPRESENTED BY THE ROBERT-KOCH-INSTITUT, Berlin (DE)

(72) Inventors: Andy Schneider, Berlin (DE); Jörg Döllinger, Berlin (DE); Peter Lasch, Berlin (DE)

(73) Assignee: FEDERAL REPUBLIC OF GERMANY LAST REPRESENTED BY THE ROBERT-KOCH-INSTITUT WHICH IS REPRESENTED BY ITS PRESIDENT, Berlin (DE)

( * ) Notice: Subject to any disclaimer, the term of this patent is extended or adjusted under 35 U.S.C. 154(b) by 309 days.

(21) Appl. No.: 16/233,193

(22) Filed: Dec. 27, 2018

(65) Prior Publication Data

US 2019/0376934 A1 Dec. 12, 2019

(30) Foreign Application Priority Data

Jun. 12, 2018 (DE) ...................... 10 2018 114 028.2

(51) Int. Cl.
*G01N 33/68* (2006.01)
*G01N 33/50* (2006.01)
(Continued)

(52) U.S. Cl.
CPC ............. *G01N 30/06* (2013.01); *C12Q 1/025* (2013.01); *G01N 30/72* (2013.01);
(Continued)

(58) Field of Classification Search
CPC .. C12Q 1/025; G01N 2030/067; G01N 30/06; G01N 30/72; G01N 33/5067;
(Continued)

(56) References Cited

U.S. PATENT DOCUMENTS

| 2002/0115201 A1* | 8/2002 | Barenburg | ............. H05B 6/806 |
| | | | 435/306.1 |
| 2007/0225246 A1* | 9/2007 | Denu | ..................... C07H 19/04 |
| | | | 514/47 |

(Continued)

FOREIGN PATENT DOCUMENTS

| EP | 2700949 A1 | 2/2014 |
| WO | 2020108802 | * 6/2020 |

OTHER PUBLICATIONS

Ravva et al. Frontiers in Cellular and Infection Microbiology, vol. 7, article 297, Jun. 30, 2017, pp. 1-8.*

(Continued)

*Primary Examiner* — Maureen Wallenhorst
(74) *Attorney, Agent, or Firm* — Nath, Goldberg & Meyer; Jerald L. Meyer

(57) ABSTRACT

A method for disrupting a sample of biological material of human, animal, or plant origin for subsequent proteome analysis by a mass spectrometry method is provided. The method involves disrupting the sample by treatment with a certain volume of an organic acid until the sample completely dissolves, incubating the sample for a certain period, and then neutralizing the sample with a neutralizing solution until a pH value between 7 and 9 is reached.

10 Claims, 3 Drawing Sheets

(51) Int. Cl.
- *G01N 30/06* (2006.01)
- *G01N 30/72* (2006.01)
- *C12Q 1/02* (2006.01)

(52) U.S. Cl.
CPC ..... *G01N 33/5067* (2013.01); *G01N 33/5097* (2013.01); *G01N 33/6848* (2013.01); *G01N 2030/067* (2013.01); *Y10T 436/24* (2015.01)

(58) Field of Classification Search
CPC ........... G01N 33/5097; G01N 33/5005; G01N 33/5094; G01N 33/6848; Y10T 436/10; Y10T 436/107497; Y10T 436/19; Y10T 436/196666; Y10T 436/20; Y10T 436/201666; Y10T 436/203332; Y10T 436/24
USPC ....... 436/8, 17, 63, 124, 126, 127, 129, 131, 436/161, 173, 174, 175
See application file for complete search history.

(56) References Cited

U.S. PATENT DOCUMENTS

| | | | |
|---|---|---|---|
| 2009/0035822 A1 | 2/2009 | Foster et al. | |
| 2014/0051113 A1* | 2/2014 | Stephenson, Jr. ... | H01J 49/0036 435/34 |
| 2015/0087003 A1* | 3/2015 | Charles .............. | G01N 33/6848 435/23 |
| 2018/0128832 A1* | 5/2018 | Isaac ........................ | G01N 1/30 |
| 2019/0086306 A1* | 3/2019 | Lopez Ferrer ....... | G01N 1/4044 |

OTHER PUBLICATIONS

Doellinger et al. Molecular & Cellular Proteomics, vol. 19, Nov. 21, 2019, pp. 209-222.*
Office Action dated May 9, 2019 issued in corresponding German Application No. 10 2018 114 028.2.
Hirano, et al. "New Protein Extraction/Solubilization Protocol for Gel-based Proteomics of Rat (Female) Whole Brain and Brain Regions", Molecule and Cells, vol. 22, No. 1, pp. 119-125, 2006.
Jiang, et al., "Comparison of protein precipitation methods for sample preparation prior to proteomic analysis", Journal of Chromatography, vol. 1023, pp. 317-320, 2004.
Zhong, et al., "Microwave-Assisted Acid Hydrolysis of Proteins Combined with Liquid Chromatography MALDI MS/MS for Protein Identification", J Am Soc Mass Spectrom, vol. 16, 471-481, 2005.
Martin, et al. "Multi-class method for biomonitoring of hair samples using gas chromatography-mass spectrometry", Anal Bioanal Chem, vol. 407, pp. 8725-8734; 2015.
Lasch, et al., "MALDI-TOF Mass Spectrometry Compatible Inactivation Method for Highly Pathogenic Microbial Cells and Spores", Anal. Chem., vol. 80, pp. 2026-2034, 2008.
Minan, et al., "Rapid identification of Burkholderia cepacia complex species including strains of the novel Taxon K, recovered from cystic fibrosis patients by intact cell MALDI-ToF mass spectrometry", Analyst, vol. 134, pp. 1138-1148, 2009.
Doellinger, et al., "Sample Preparation by Easy Extraction and Digestion (SPEED)—A Universal, Rapid, and Detergent-free Protocol for Proteomics based on Acid Extraction", bioRxiv, Aug. 16, 2018.
International Search Report dated Jan. 31, 2019 issued in corresponding International Application No. PCT/EP2018/080987.

* cited by examiner

SAMPLE PREPARATION FOR PROTEOMIC INVESTIGATIONS

The invention relates to a method for processing biological material for proteomic investigations, involving lysis of the material using an organic acid.

The proteome comprises the entirety of all proteins expressed in a cell or a living organism at a particular time under certain conditions. The field concerned with the analysis of the proteome is referred to as proteomics, the central technology of which is currently liquid chromatography coupled with mass spectrometry (LC-MS). Owing to the huge significance of proteins for the phenotype of living organisms, proteomic techniques are increasingly widely used within medicine and the life sciences, including for the identification of diseases biomarkers or for the future tailoring of therapy methods to patients on an individual basis.

In this connection, different sample materials such as cells, tissues or body fluids place high demands on preparation techniques for proteomics, and what are striven for are simple, rapid, robust and reproducible methods of sample preparation. In the case of bottom-up proteomics, these substantially comprise three essential steps: (i) lysis/extraction, (ii) digestion and (iii) peptide purification. Depending on the nature of the sample material, the technique used and the experimental strategy, sample preparation can be expanded by additional steps, such as, for example, purification steps or labeling-reaction steps.

The current state of technology is based on the extraction of proteins by means of detergents (e.g., sodium lauryl sulfate (SDS), deoxycholic acid (SDC)) and/or chaotropic substances (e.g., urea, guanidine hydrochloride (GnHCl)), frequently supported by input of physical energy (ultrasound, pressure, friction, grinding, heat) in order to achieve an effective lysis of the sample material.

Especially in the case of difficult-to-disrupt samples (e.g., tissue with a high proportion of collagen), there is frequently the need for further working steps or for the use of additional reagents. However, the presence of said reagents can have an adverse effect on the efficiency of subsequent preparation steps (digestion), and so standard protocols of bottom-up proteomics contain, in many cases, further procedures for removing detergents, chaotropic substances and similar active substances. At the same time, the additional working steps generally have an adverse effect on reproducibility and protein yield. However, against the background of the huge potential of proteomics, for example within the scope of personalized medicine, what is striven for is a simple, direct, reproducible and automatable method of sample preparation.

This object is achieved by a method according to the invention having the features of claim 1. Further advantageous embodiments and configurations of the invention are apparent from the additional independent claims and the dependent claims, from the figures and from the exemplary embodiments. It is possible to combine the embodiments of the invention with one another in an advantageous manner. Alterations and modifications of the invention that are obvious to a person skilled in the art are covered by the scope of protection of the claims.

A first aspect of the invention relates to a method for disrupting a sample of biological material for proteome analysis by a mass-spectrometry method, comprising the following working steps:
  providing the sample in a reaction vessel,
  adding a certain amount of an organic acid to the sample,
  incubating the preparation,
  adding a neutralizing solution to the preparation.

The method according to the invention is advantageous because fewer working steps are required in comparison with conventional methods. Thus, it is more economical in terms of time and effort than conventional methods. Furthermore, a greater intensity of signals with a lower variance are advantageously obtained using sample material disrupted according to the invention in comparison with conventional methods (FIG. 3). A further advantage is a high reproducibility of the method, this being essential particularly with regard to quantitative analyses. Furthermore, proteins are highly stable in such solutions with a high salt concentration, and this considerably facilitates transport, storage and archiving of the samples.

Moreover, it is advantageously possible to use the method for any type of biological material containing proteins which are to be analyzed by proteomics techniques. Preferably, the biological material encompasses samples of human, animal or plant origin, especially tissues, cells, body fluids, blood and blood products, swabs as well as feces.

The biological material is provided in an appropriately sized reaction vessel made of an appropriate material. Standard vessels made of plastic with a volume of up to 2 ml are advantageous, for example so-called microreaction tubes, which are commonly used in laboratories.

The amount of organic acid to be added is at the discretion of a person skilled in the art. For a known amount of biological material, a standardized amount of acid is ideally added. Ideally, a sample-to-acid ratio is set such that the sample material completely dissolves.

The sample material can be readily incubated at room temperature with the acid for up to 60 min without the quality of the proteins suffering. In this connection, the lysis can be ended once the suspension becomes clear, this being the case after 2-10 min for the majority of samples.

The sample is neutralized in order to prepare the proteins for digestion. Neutralization is carried out by using a weak base, for example an aqueous 2 M TRIS solution (tris (hydroxymethyl)aminomethane), and the volume of the TRIS solution ought to be about 7-15 times the sample volume. What is striven for in this connection is a pH between 7 and 9, ideally between 8 and 8.5.

Preferably, the method comprises an additional step of electromagnetic irradiation directly before the neutralization. Said step is particularly advantageous for difficult-to-disrupt samples, for example samples with a high proportion of collagen. A thermal treatment at temperatures >40° C. shows comparable effects.

Particularly preferably, the sample is irradiated by microwaves. In this connection, the sample is exposed to a microwave output of 800 W for a period of 5-30 s, especially for 10 s. It is advantageous to surround the reaction vessel in which the sample is incubated with an additional shell, for example a further vessel made of plastic. It has been found that the microwave treatment is advantageous for an effective lysis for any type of biological material, but especially for difficult-to-lyse material.

Preferably, the organic acid used in the method is a carboxylic acid. Even more preferably, a haloacid is used in the method. Particularly preferably, the organic acid used in the method is trifluoroacetic acid (TFA) and the derivatives thereof. It has become apparent that TFA is particularly effective in the lysis of tissues and cells. At the same time, the use of TFA is also advantageous because the analysis of the proteins is not impaired by the action of the TFA.

Furthermore, the method preferably comprises the further steps of:
adding an alkylation solution,
adding a reduction solution,
determining the protein concentration,
diluting the sample with water,
enzymatically or chemically cleaving the proteins,
purifying the peptides generated.

A second aspect of the invention relates to the use of trifluoroacetic acid for the lysis of biological material. In this connection, TFA is suitable for any above-mentioned biological material.

A third aspect of the invention relates to the use of a sample of biological material, which was prepared by means of the method according to the invention, by a mass-spectrometry method.

The advantages of said uses correspond to the advantages of the method according to the invention.

The invention will be more particularly elucidated with reference to the figures, where:

Figure 1:
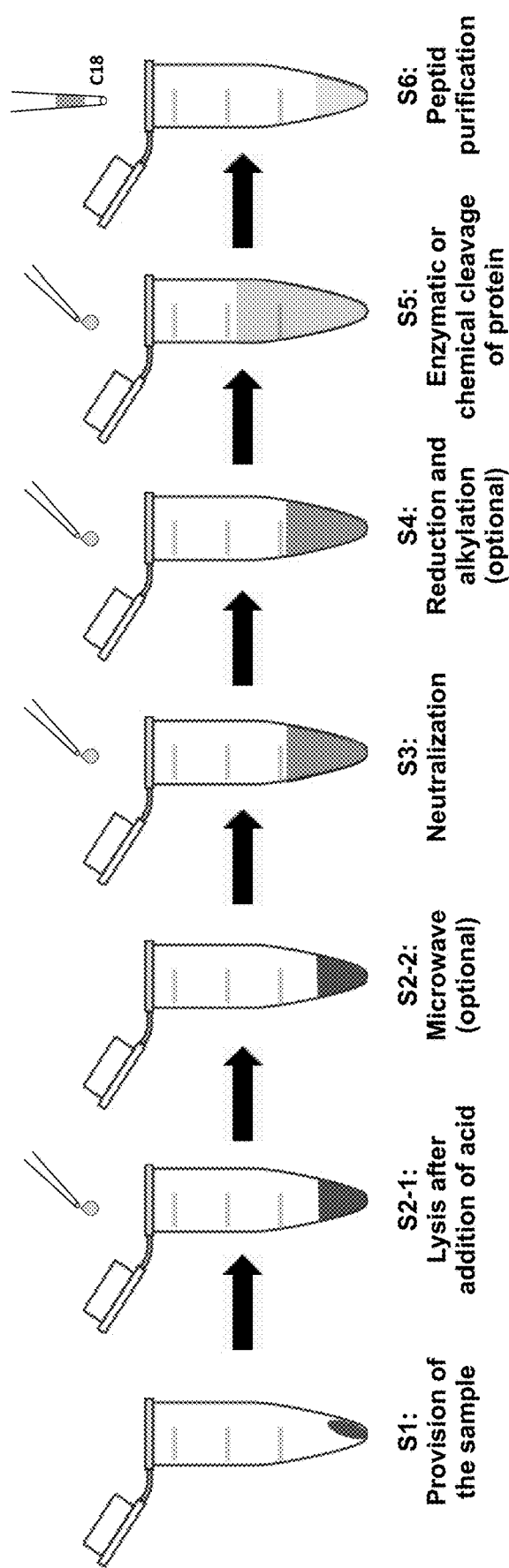
FIG. 1 shows a flow chart of one embodiment of the method according to the invention.

In one embodiment of the method according to the invention as per the depiction in FIG. 1, a sample of a biological material is provided in a first step S1. The biological material can be a tissue sample, for example a blood sample, or a suspension or a pellet of cells and also solid tissue structures.

Figure 2:
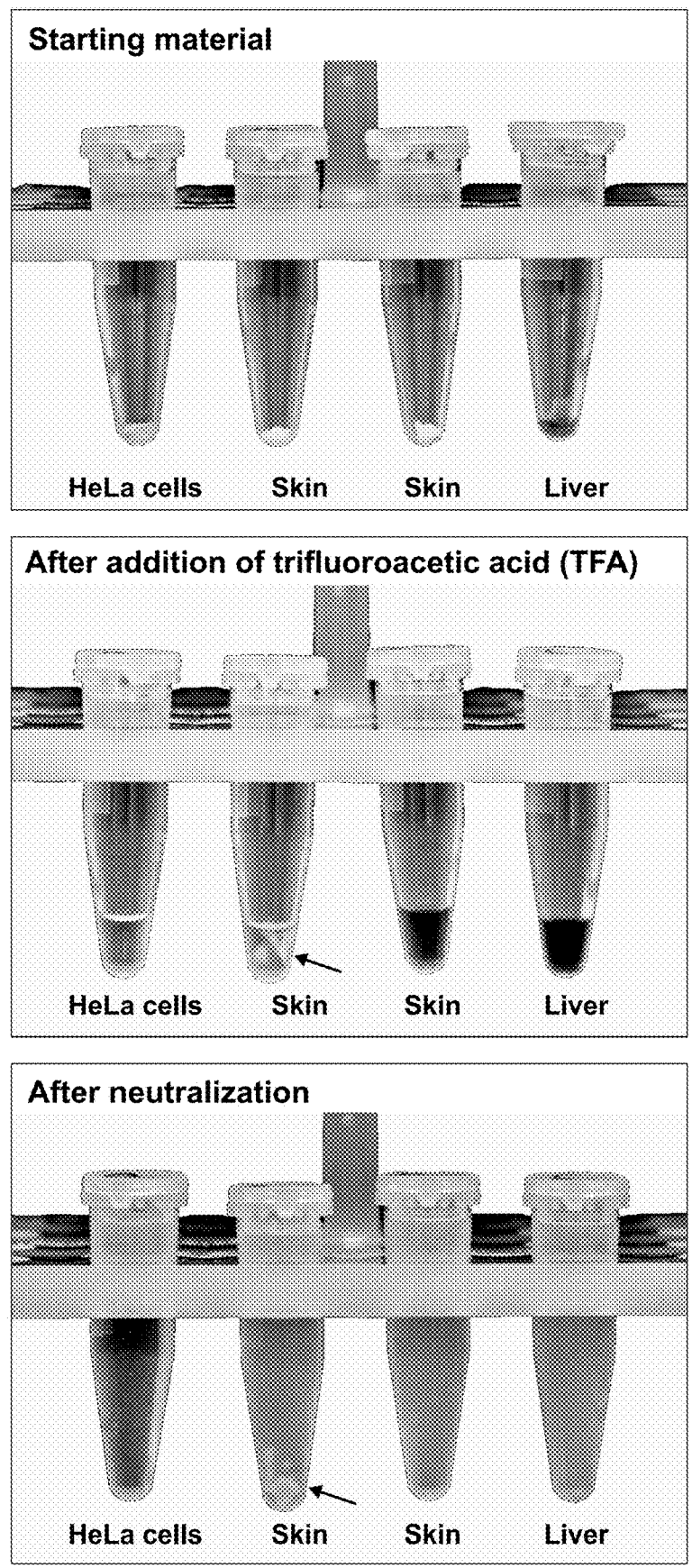
FIG. 2 shows a comparison of the lysis of samples.

In a second step S2-1, pure trifluoroacetic acid is added in excess to the biological material, ideally in a volume ratio between 1:1-1:10 (sample to TFA). The preparation is mixed, for example by means of a vortexer, and incubated at room temperature for 1-10 min. In the course of this, the sample material is lysed. In addition to the chronological sequence, the course of lysis is followed visually; when the solution becomes clear, the sample material has been lysed (FIG. 2). If the protein concentration is too high for extraction with the specified amount of acid, an appropriate further volume of acid is added, for example 100 µl. In an optional step S2-2, which supports the disruption of difficult-to-lyse materials, the material is incubated in a microwave at an output of 800 W for 10 s.

To illustrate the action of acid on the samples, FIG. 2 depicts various sample types, before and after lysis in each case. Depicted from left to right are: a suspension of HeLa cells (human), two skin samples (chicken) and one liver sample (chicken). Depicted in each case are the starting material as well as the samples after lysis with TFA and after performance of neutralization. Whereas the HeLa cells and the liver tissue are completely lysed by sole addition of acid, undissolved tissue constituents become apparent in one of the skin samples (second sample from the left; see the arrows) after addition of TFA and after neutralization. Said constituents can be dissolved when the sample is irradiated with microwaves (Skin* sample; see the third sample from the left).

After the solution becomes clear, the lysed material preparation is neutralized with an aqueous 2 M TRIS solution in a third step S3. In this connection, one volume of the sample is neutralized by adding about 8-15 times the volume of a 2 M TRIS solution, i.e., for a 100 µl lysis preparation, 1000 µl of 2 M TRIS solution are added.

In any case, the pH of the solution is checked in step S3. What is striven for in this connection is a pH between 7 and 9, ideally between 8 and 8.5. To reach the striven-for pH, readjustment is carried out if necessary by adding 2 M TRIS or a diluted trifluoroacetic acid solution until the optimum pH is reached.

After the neutralization, the solution is admixed with a reduction and alkylation solution in a fourth step S4. To this end, a freshly prepared solution of 100 mM TCEP (tris(2-carboxyethyl)phosphine) and 400 mM CAA (chloroacetamide) in water is used, of which 10% of the sample volume are added to the sample. The samples are incubated in a thermal mixer at 95° C. for a period of at least 3-10 min. After this step, the samples can be frozen and can be stored at temperatures ≤−20° C. for a relatively long period. Step S4 can be omitted if peptides containing no cysteines are being analyzed. It is also possible to use alternative reduction and alkylation reagents, such as, for example, DTT (dithiothreitol) or IAA (iodoacetamide), and in this case the incubation conditions must be adjusted accordingly.

In a fifth step S5, the method is continued by cleaving the proteins of the sample enzymatically or chemically into peptides. To this end, in the case of an enzymatic digestion, the protein concentration of the sample is determined in a manner known to a person skilled in the art, and trypsin or another suitable enzyme is then added to the sample in a defined mass ratio, this being within the range from 500:1 to 5:1 for trypsin (protein:trypsin). The sample can be diluted with water according to the dependence of the activity of the enzyme used on the buffer concentration of the lysate. The digest preparation is then incubated at a temperature optimum for the enzyme (37° C. for trypsin) for an appropriate length of time (1-24 h for trypsin).

In a sixth step S6, the peptides are purified, for example by a solid-phase extraction on C18 material.

Figure 3:
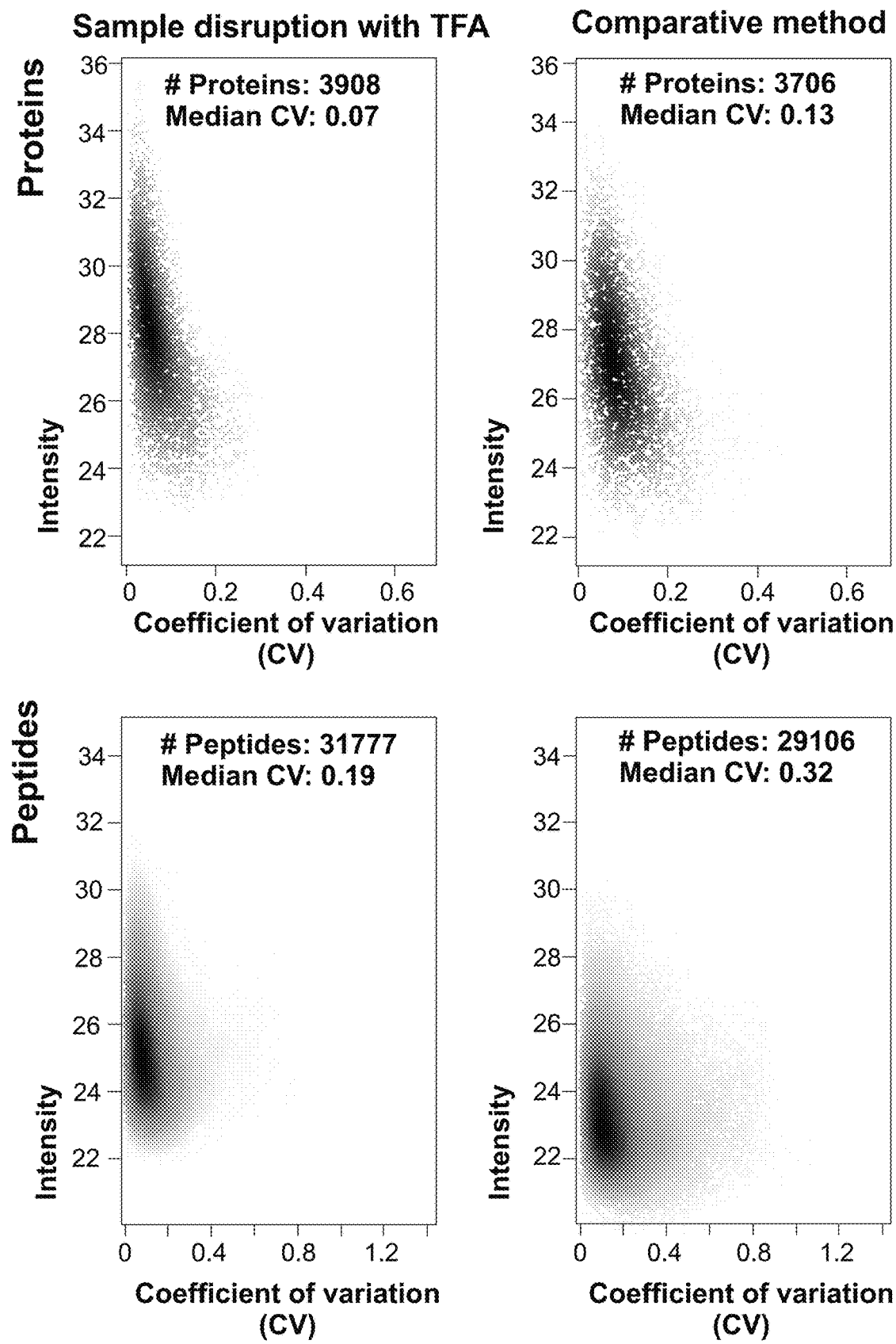
FIG. 3 shows results of a proteome analysis of human cells from the described method in comparison with a reference method (triplicates).

The purified peptides can then be analyzed by means of liquid chromatography coupled with mass spectrometry (LC-MS) or using comparable methods such as capillary electrophoresis coupled with mass spectrometry. FIG. 3 depicts a comparison of the results of a proteome investigation of human cells with an alternative sample preparation method. For this purpose, the coefficient of variation (CV) was shown against the signal intensity for peptides and for the resulting proteins in a scatter plot. The cloud of points was overlaid with a heat map. The number of quantified peptides and proteins as well as the mean values of the CVs are likewise indicated. On the left-hand side, the graphs depict results from a sample which was disrupted using the method according to the invention as per FIG. 1, and the graphs on the right-hand side show results from a sample disrupted using conventional methods. It can be seen that more peptides and, derived therefrom, more proteins can be captured at a lower signal variance using the method according to the invention than using a conventional method.

What is claimed is:

1. A method for disrupting a sample of biological material for proteome analysis by a mass-spectrometry method, comprising the steps of:
   providing the sample in a reaction vessel, wherein the biological material of the sample is selected from the group consisting of human biological material, animal biological material, and plant biological material;
   adding a certain amount of an organic acid to the sample until the biological material of the sample completely dissolves;

incubating the sample; and adding a neutralizing solution to the sample until a pH between 7 and 9 is reached.

2. The method as claimed in claim 1, wherein the sample is selected from the group consisting of a tissue sample, a cell sample, a sample of body fluids, a blood sample, a sample of blood products, a swab sample, and a fecal sample.

3. The method as claimed in claim 1, wherein the method comprises the additional step of electromagnetic irradiation or of heating of the sample directly before the step of adding the neutralizing solution.

4. The method as claimed in claim 3, wherein the irradiation carried out is a microwave irradiation or the sample is heated to over 40° C.

5. The method as claimed in claim 1, wherein the organic acid used is a carboxylic acid.

6. The method as claimed in claim 1, wherein the organic acid used is a haloacid.

7. The method as claimed in claim 1, wherein the organic acid used is trifluoroacetic acid.

8. The method as claimed in claim 1, wherein, following the step of adding the neutralizing solution, the method further comprises the steps of:

adding an alkylation solution to the sample;

adding a reduction solution to the sample;

determining a concentration of proteins in the sample;

diluting the sample with water;

enzymatically or chemically cleaving the proteins in the sample; and purifying peptides generated thereby.

9. A method for conducting mass spectrometry on a biological material of human, animal or plant origin, comprising:

obtaining the biological material according to the method of claim 1; and conducting mass spectrometry on the obtained biological material.

10. A method for disrupting a biological material of human, animal or plant origin, comprising:

adding trifluoroacetic acid to the biological material; and disrupting the biological material with the trifluoroacetic acid, wherein the trifluoroacetic acid is added until the biological material completely dissolves.

\* \* \* \* \*